US005361781A

United States Patent [19]
Antonini

[11] Patent Number: 5,361,781
[45] Date of Patent: Nov. 8, 1994

[54] DEVICE FOR REMOVAL AND DISPOSAL OF A CHEST DRAIN

[76] Inventor: Thomas J. Antonini, 111 Wilshire Rd., Syracuse, N.Y. 13209-2248

[21] Appl. No.: 40,915

[22] Filed: Mar. 30, 1993

[51] Int. Cl.$^5$ .......................... A61B 19/00; A61F 5/37
[52] U.S. Cl. ...................... 128/849; 128/846; 128/853; 128/854
[58] Field of Search ............... 128/846, 847, 849–856, 128/DIG. 26, DIG. 6; 604/303, 307, 174, 177–180; 602/903

[56] References Cited

U.S. PATENT DOCUMENTS

| | | |
|---|---|---|
| 3,030,957 | 4/1962 | Melges . |
| 3,542,019 | 11/1970 | Gittins . |
| 3,625,205 | 12/1971 | Madden et al. ............ 128/855 |
| 3,668,050 | 6/1972 | Donnelly ................... 128/852 |
| 3,878,843 | 4/1975 | Morgan . |
| 3,916,887 | 11/1975 | Kelly . |
| 4,042,109 | 8/1977 | Barcan . |
| 4,314,558 | 2/1982 | Korpman . |
| 4,324,237 | 4/1982 | Buttaravoli . |
| 4,374,520 | 2/1983 | Grossmann et al. . |
| 4,784,656 | 11/1988 | Christian . |
| 4,973,314 | 11/1990 | Garrett ............. 128/DIG. 26 |
| 5,013,307 | 5/1991 | Broida . |
| 5,080,108 | 1/1992 | Roth ......................... 128/849 |

FOREIGN PATENT DOCUMENTS 1261390  1/1972  United Kingdom ........ 128/849

Primary Examiner—Randall L. Green
Assistant Examiner—P. Zuttarelli
Attorney, Agent, or Firm—Harris Beach & Wilcox

[57] ABSTRACT

Apparatus for use in the sanitary removal from a patient's body and disposal of an indwelling tube wherein a sheet of flaccid material is brought to the exit site and formed into a pouch enclosing the exterior end of the tube. The pouch is gathered about the exterior end of the tube and the implanted end of the tube. A flap is placed over the exit site and the tube is pulled into the pouch as it is ungathered so as to prevent the unwanted broadcasting of potentially infectious body fluids which might otherwise contaminate the health care worker or other patients.

3 Claims, 3 Drawing Sheets

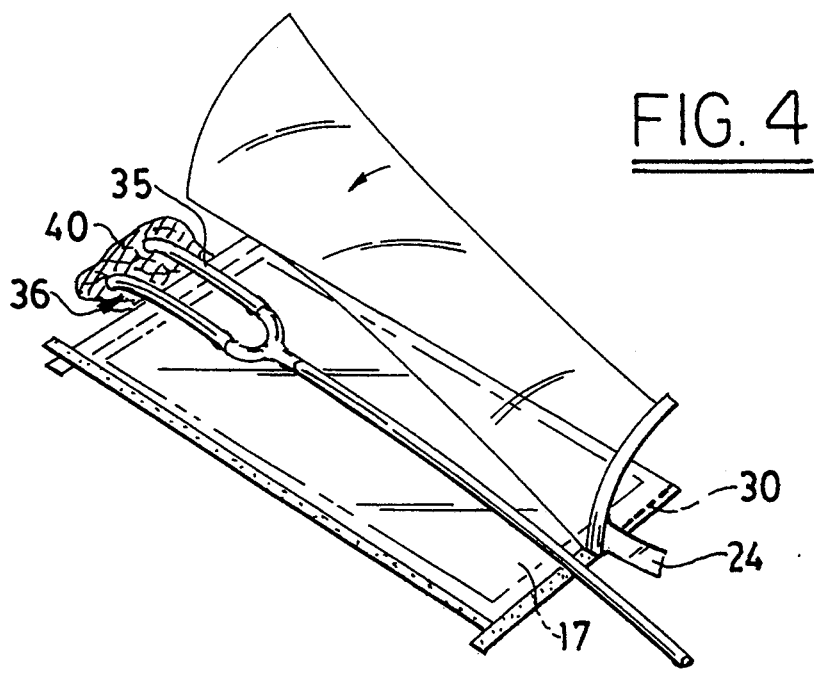
FIG. 4
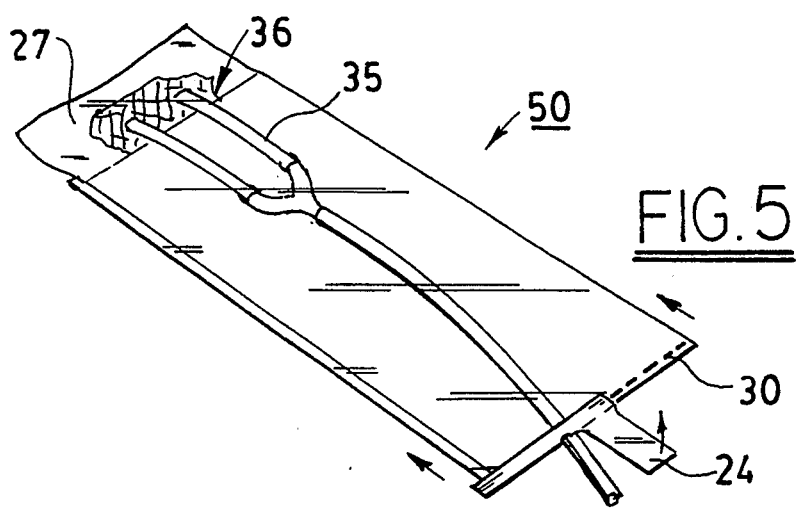
FIG. 5
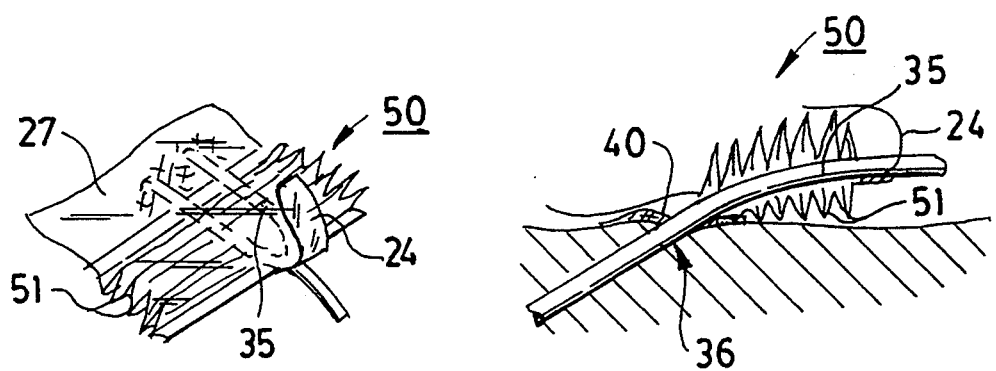
FIG. 6
FIG. 7

DEVICE FOR REMOVAL AND DISPOSAL OF A CHEST DRAIN

BACKGROUND OF THE INVENTION

This invention relates to method and apparatus for aseptic removal and disposal of a drainage tube or the like that is implanted in a human body.

With the spread of the HIV virus and other contagious diseases that are readily carried by body fluids, the protection of health care workers treating potentially infected patients has become of paramount concern. In many situations the health care worker is unaware of whether a particular patient is infected with one of these highly contagious diseases. The utmost of care must therefor be exercised when treating any patient. As is well known, a good deal of blood and other body fluids are typically broadcast when implanted body drains, catheters or the like are removed from a patient. The sanitary removal and disposal of chest drains, in particular, can be extremely difficult because of the amount of body fluid that is usually present at the drainage site.

Drapes are sometimes used during certain medical and surgical procedures to provide a clean field for carrying out the procedure. The drape is typically used to cover a portion of the patient's body around the site and an opening is formed immediately over the site to provide access thereto. The non-sterile drape usually contains one or more absorbent layers so that any fluids escaping from the site are trapped in the layer and the soiled drape is disposed of by depositing it in a suitable infectious waste container. These drapes, however, are not readily adapted for use in protecting health care workers when removing implanted body tubes. Buttaravoli, in U.S. Pat. No. 4,324,237, describes a drape-like device that is adapted to be used as a dressing and a means of securing a catheter at the wound or exit site. The drape, however, offers no protection to the health care worker, nor does it help in the sanitary disposal of the catheter.

SUMMARY OF THE INVENTION

It is therefor an object of the present invention to contain body fluids adherent to indwelling tubes when removing implanted drains and the like, It is a further object of the present invention to provide a protective device for facilitating sanitary removal and disposal of an implanted body drain.

A still further object of the present invention is to provide a containment device that is particularly well suited for use in removing and disposing of one or more implanted chest drains.

Another object of the present invention is to prevent the spread of infectious disease through unwanted contact with contaminated body fluids.

These and other objects of the present invention are attained by means of a thin sheet of plastic that is foldable along a central axis into two half-sections. The top surface of a first half-section has adhesive strips located along the peripheral edges. A strip of medical adhesive tape is mounted on the bottom of the first half-section along the upper edge thereof which is used to secure the device to a patient's chest, In practice, the first half-section is adhesively secured to the patient's body adjacent the exit site of an implanted tube and the exterior end of the tube is placed upon the first half-section. The second half-section is folded over the first along the central axis and is adhesively secured thereto using the adhesive edge strips to form a pouch. An outwardly extended flap is connected to the second half-section along its upper edge which covers the exit site, The pouch is then gathered over the exterior end of the tube. Both the tube and the lower section of the gathered pouch are grasped with one hand and the implanted end of the tube is firmly pulled into the pouch while holding the flap end of the pouch stationary with the other hand. A hand-engageable tab is secured to the lower end of the pouch to help the user in pulling the gathered pouch away from the exit site. Once the tube is completely contained within the pouch, the pouch is removed from the patient and the flap is folded under the first half-section and is sealed against the now exposed medical tape. The pouch with the enclosed tube is then disposed of in a normal, yet sanitary manner.

BRIEF DESCRIPTION OF THE DRAWINGS

For a better understanding of these and other objects of the present invention, reference will be made to the following detailed description of the invention which is to be read in conjunction with the accompanying drawings, wherein:

FIG. 4 is a perspective view of the present device showing it being positioned at an exit site adjacent to the exterior end of an implanted drain;

FIG. 5 is a perspective view showing the device folded into a pouch with the exterior end of the drain enclosed in the pouch;

FIG. 6 is a perspective view showing the pouch accordion-folded into a compressed package over the exterior end of the drain;

FIG. 7 is a side elevation in partial section showing the compressed pouch;

DESCRIPTION OF THE INVENTION

Figure 1:
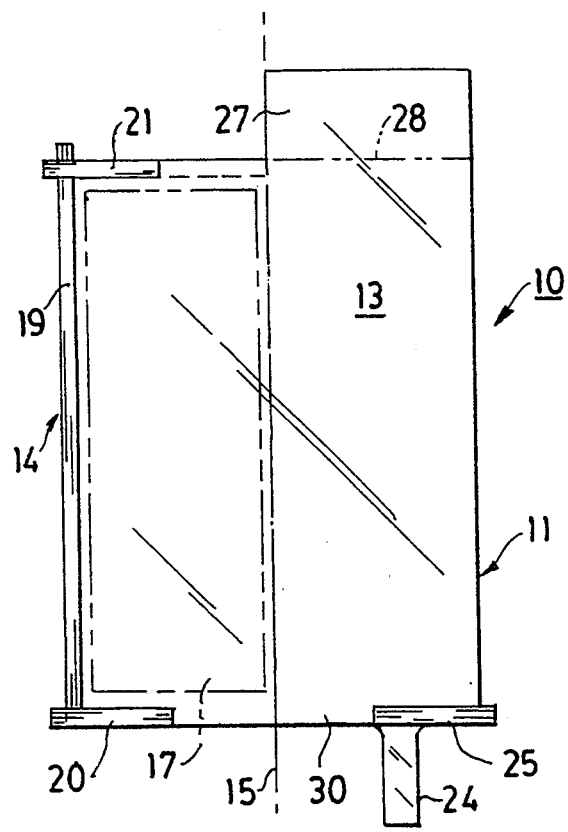
FIG. 1 is a top plan view showing the present invention.
Figure 2:
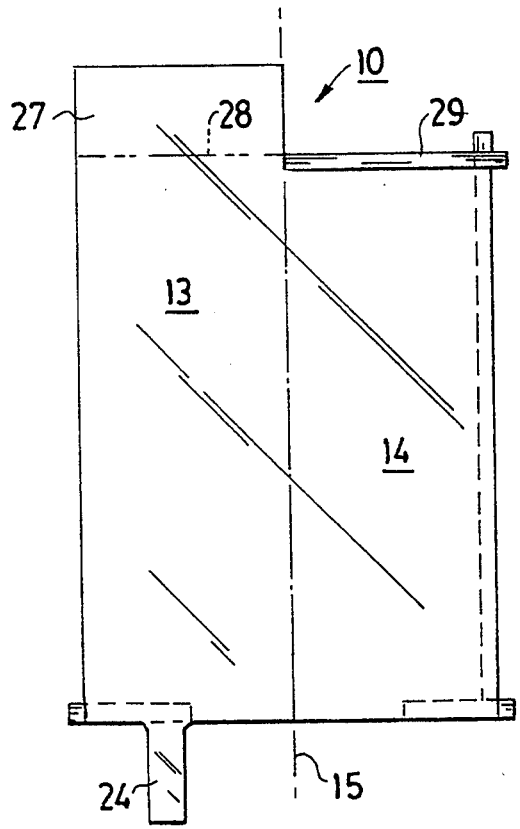
FIG. 2 is a bottom view of the device shown in FIG. 1.
Figure 3:
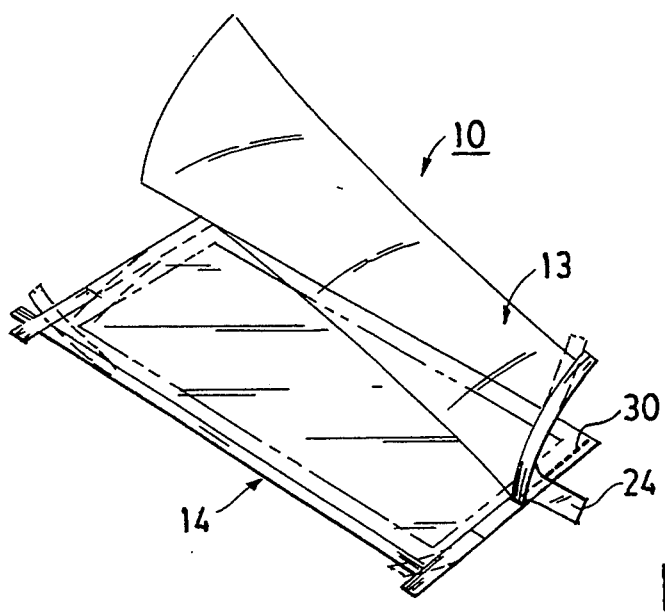
FIG. 3 is a perspective view of the device shown in FIGS. 1 and 2 further illustrating one half of the device being folded over the other half-section.
Figure 8:
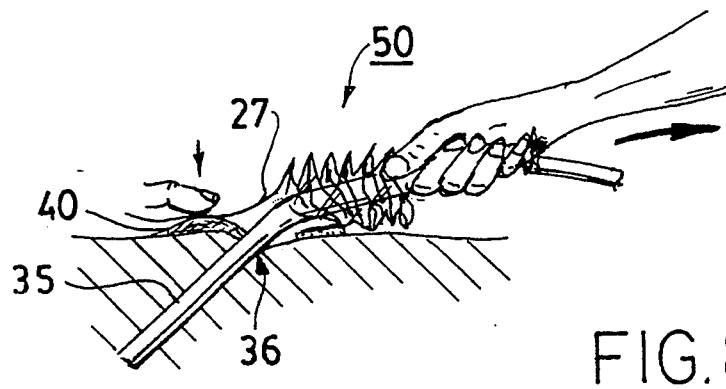
FIG. 8 illustrates the hand position of the user just prior to removal of the implanted end of the drain.

Referring initially to FIGS. 1–3, there is shown the preferred embodiment of the present invention which will be described for use in the removal and disposal of a chest drain. It should be clear, however, that the present invention is suitable for use in removing and disposing of any indwelling device. The present device, generally referenced 10, includes a thin base sheet of flaccid transparent plastic material 11. The sheet is divided into a first half-section 13 and a second half-section 14 along a central axis or fold line 15. The first half-section may include a pad 17 which is shown in phantom outline. The pad, if used, is made of a highly absorbent material bonded to its top surface with the pad extending substantially along the length of the half-section adjacent to the central axis.

The first half-section 14 further includes a first adhesive strip 19 mounted upon the top surface of the sheet along the peripheral side edge thereof. A second adhesive strip 20 is also mounted upon the top surface of the sheet that extends along the lower peripheral edge of the half-section. A third strip of adhesive 21 is similarly mounted on the top surface of the first half-section along the upper peripheral edge thereof from the outer edge of the base sheet to the absorbent pad. As illustrated in FIG. 2, a strip of medical adhesive tape 29 is mounted on the back side of the first half-section along its entire upper edge. Each of the adhesive strips and the medical tape are provided with a protective covering that is removed prior to using the device.

The second half-section 13 contains a downwardly disposed tab 24 that is integral with the base sheet. An adhesive strip 25 is located along the inside lower edge of the second half-section to provide additional adhesive strength in this area. A flap 27, which is also integral with the base sheet, extends outwardly from the upper edge of the second half-section along fold line 28.

As shown in FIGS. 3 and 5, the two half-sections can be folded over to create a pouch for housing one or more chest drains or other indwelling devices.

In the main embodiment of the invention, the two half-sections may be initially folded along the fold line 15 and the seam area between the half-sections designated at 30 in FIGS. 1 and 5 is heat bonded to create a semi-closed pouch. The main embodiment of the invention will be explained in greater detail below with reference to a removal and disposal device that employs both heat and adhesive bonded seams to seal the edge regions of the folded half-sections. However, it should be clear to one skilled in the art that the heat bonded seam can be replaced with an adhesive seam without departing from the teachings of the present invention.

Turning now more specifically to FIGS. 4–10, the utilization of the present invention will be described with reference to a drain 35 that is implanted within a patient's chest at an exit site 36. Initially, the upper edge of the first half-section is placed adjacent to the exit site 36 with the exterior end of the drain 35 next to the absorbent pad 17. A sterile dressing 40 is placed around the exit site (FIG. 4) and the protective coverings of the adhesive strips and the medical tape are removed. The medical tape 29 is then adhesively secured to the patient's chest to hold the device in place at the exit site.

The second half-section 18 is now folded over the first half-section 13 with the exterior end of the drain lying between the two half-sections. The opposing lateral edges of the two sections are adhesively sealed using the adhesive edge strips to create an enclosed pouch 50 (FIG. 5). The extended flap 27 is placed over the exit site.

Figure 9:
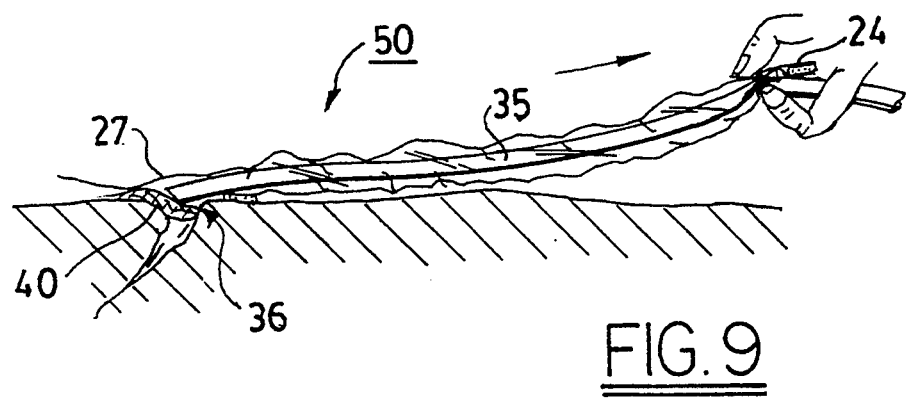
FIG. 9 illustrates the implanted end of the drain being drawn into the pouch.
Figure 10:
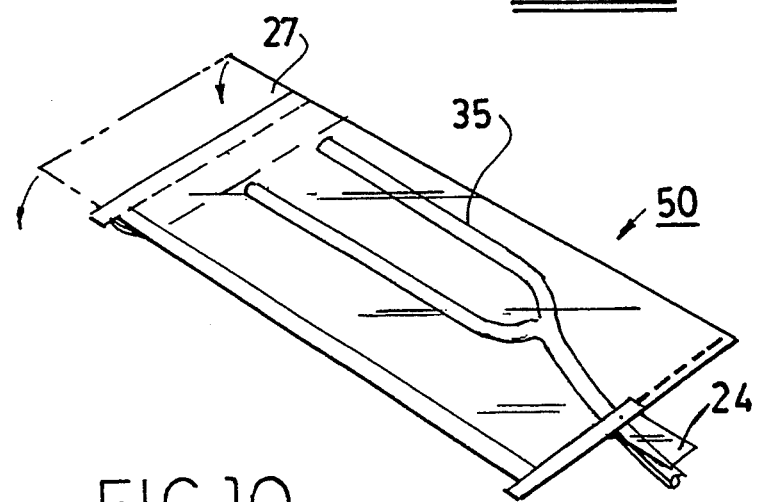
FIG. 10 illustrates the drain completely enclosed in the pouch and the pouch in a condition for disposal.

As shown in FIGS. 6 and 7, the pouch is now compressed or gathered into folds 51—51 about the exterior end of the drain. The user then grasps the lower edge of the pouch including tab 24, and while holding the upper portion of the pouch and the flap stationary (FIG. 8) firmly pulls the drain from the exit site into the pouch (FIG. 9). When the drain is fully enclosed within the pouch (FIG. 10) the pouch is removed from the patient's chest and the flap is folded under the pouch and sealed against the medical adhesive strip located on the bottom surface thereof. As can be seen, the previously implanted section of the drain is now fully enclosed within the pouch. The drain and the pouch are then safely disposed of by placing them in an approved infectious waste container.

While this invention has been explained with reference to the structure disclosed herein, it is not confined to the details set forth and this application is intended to cover any modifications and changes as may come within the scope of the following claims:

What is claimed is

1. Apparatus for facilitating the safe and sanitary removal of a drain implanted in a patient's chest cavity through an incision that includes:
   a flaccid rectangular plastic sheet having a front surface and a back surface, a top edge and a bottom edge and two opposed side edges, said sheet being divided along a vertical fold line into first and second half sections whereby the first half section can be placed beneath a portion of a chest implanted drain and the second half-section folded along the fold line over the first half section to create a flaccid pouch that is open along the folded top and bottom edges of the sheet,
   a first adhesive strip mounted upon the back surface of the sheet adjacent to the top edge of the first half section whereby the first section can be adhesively attached to the chest of a patient next to an incision through which the drain is implanted,
   a second adhesive strip mounted on the front surface of the sheet adjacent to one of the side edges to adhesively close the pouch over a portion of the drain, and
   a flap integral with the second half section that depends upwardly from the top edge thereof to cover the incision,
   whereby the pouch can be pleated along the drain toward the incision and the implanted portion of the drain drawn into the pouch as the drain and the pouch are pulled simultaneously away from the incision.

2. The apparatus of claim 1 that further includes a tab means integral with one of the half sections that depends downwardly from the bottom edge thereof that can be grasped with the drain to facilitate pulling of the drain and the pouch away from the incision.

3. The apparatus of claim 2 that further includes a third adhesive strip mounted on the front surface of the sheet adjacent to the bottom edge of one of the half sections for adhesively closing a portion of the bottom opening in the pouch.

* * * * *